United States Patent [19]

Richards

[11] Patent Number: 5,344,405
[45] Date of Patent: Sep. 6, 1994

[54] SINGLE-USE SYRINGE

[76] Inventor: Donald C. Richards, P.O. Box 685, Walpole, N.H. 03608

[21] Appl. No.: 118,583

[22] Filed: Sep. 10, 1993

[51] Int. Cl.$^5$ .............................................. A61M 5/00
[52] U.S. Cl. ................................... 604/110; 604/198; 604/218
[58] Field of Search ............... 604/110, 187, 198, 218, 604/232, 263

[56] References Cited

U.S. PATENT DOCUMENTS

| | | |
|---|---|---|
| 2,571,653 | 10/1951 | Bastien . |
| 3,306,290 | 2/1967 | Weltman . |
| 3,672,368 | 6/1972 | Schwarz . |
| 3,890,971 | 6/1975 | Leeson et al. . |
| 4,631,057 | 12/1986 | Mitchell . |
| 4,804,372 | 2/1989 | Laico et al. . |
| 5,049,133 | 9/1991 | Villen Pascual . |
| 5,061,251 | 10/1991 | Juhasz . |
| 5,084,029 | 1/1992 | Nacci nee Tagliafferi et al. . |
| 5,135,510 | 8/1992 | Maszkiewicz et al. .......... 604/198 X |
| 5,201,708 | 4/1993 | Martin ................................. 604/110 |
| 5,201,720 | 4/1993 | Borgia et al. ........................ 604/198 |

Primary Examiner—John D. Yasko
Attorney, Agent, or Firm—Richard C. Litman

[57] ABSTRACT

A single-use syringe having a needle which retracts upon a full depression of its plunger and thus, renders the syringe non-reusable. The plunger selectively engages the barrel of the syringe so as to limit the withdraw of the plunger relative to the barrel. The barrel has formations extending therefrom which selectively and matingly engage formations extending from the plunger so as to selectively limit the travel of the plunger relative to the needle and retract the needle into a concealed position. The nose of the barrel carries a split ring which is contractible to permit a rearward displacement of the barrel and the needle attached thereto relative to the stationary housing upon a full depression of the plunger. The travel of the barrel relative to the stationary body is terminated by dogs located proximate the forward end of the nose which are engageable with the notches in the stationary housing upon the rearward displacement of the barrel relative to the stationary housing. A cap may be provided for sheathing the needle prior to use.

19 Claims, 6 Drawing Sheets

SINGLE-USE SYRINGE

BACKGROUND OF THE INVENTION

1. Field of the Invention

The present invention relates to a syringe and, more particularly, to a syringe having a needle which retracts upon a full depression of its plunger, rendering the syringe non-reusable.

2. Description of the Prior Art

Health care professionals who work in proximity to hypodermic needle type syringe devices are susceptible to accidental and potentially infectious contact with contaminated syringe needles resulting from careless handling and disposal of the same after use. Moreover, the spread of infectious diseases has reached epidemic proportions among users of controlled substances who exchange syringes. To combat the spread of disease on both fronts, there is a need to prevent both accidental needle strikes from as well as repeat usage of a syringe. This invention provides that protection automatically.

Several attempts have been devised to meet this end. For example, U.S. Pat. No. 2,571,653, issued Oct. 16, 1951 to Victor G. Bastien, discloses a syringe cover which may be snap-locked in an extended position after use to sheath the needle and offer protection against accidental needle strikes. The syringe cover proposed by Bastien must be extended manually as opposed to being automatically extended to sheath the needle. Moreover, this syringe cover may be retracted after use to expose the needle for reuse.

An automatically retractable syringe needle is disclosed in U.S. Pat. No. 3,306,290, issued Feb. 28, 1967 to Harold S. Weltman. Unlike applicant's instant invention, Weltman does not discloses a syringe in which the needle is conditionally fixed in an initially extended position where it can be covered with a protective cap. Further, Weltman does not disclose a needle which is retracted from the conditionally fixed position upon a full depression of the plunger and is retained in this retracted position so as to be non-reusable.

A syringe is disclosed in U.S. Pat. No. 3,672,368, issued Jun. 27, 1972 to Lothar Schwarz, wherein the syringe has a plunger for advancing a plug forward to empty a cartridge through a needle. An auxiliary plunger slides a needle forward into an operating position and an arresting device engages the needle to retain the needle in an advanced position. The actuating and auxiliary plungers are operated independent of one another. Further, the needle is not retractable and retained in a retracted position after use.

U.S. Pat. No. 3,890,971, issued Jun. 24, 1975 to Thomas A. Leeson et al., discloses a single-use syringe having a slidable needle cap which is mounted over the needle end of the barrel housing and is movable inwardly in order to expose the needle. A cap safety lock means is provided for moving the protective cap outwardly over the needle and locking the cap against further inward movement after the syringe has been used.

A shielded needle is disclosed in U.S. Pat. No. 4,631,057, issued Dec. 23, 1986 to Charles B. Mitchell, wherein the shielded needle comprises a body, a needle coupled to the body, and a needle guard mounted on the body for movement from a retracted position in which the guard does not shield the needle to an extended position in which the guard shields the needle. The guard can be releasably retained in the retracted position and locked in the extended position. Mitchell does infer that force can be applied to retract the needle guard after use and expose it for reuse.

A protective needle sheath is disclosed in U.S. Pat. No. 4,804,372, issued Feb. 14, 1989 to Joseph P. Laico et al. The sheath is manually extendable for protecting the sharpened needle point of a hypodermic needle. The sheath comprises a pair of telescopic enclosure shields mounted to the needle base. Detent locking members lock the shields in a non-retractable protective position.

Another single-use safety syringe in disclosed in U.S. Pat. No. 5,049,133, issued Sep. 17, 1991 to Joeé A. Villen Pascual, who teaches a syringe provided with a needle and a spring coiled around the needle wherein the spring is capable of expanding upon a full depression of the plunger to retract the needle into the body of the syringe. The syringe includes means for retaining the needle in a position for use and for preventing the needle from moving after use. The plunger can be withdrawn to fill the barrel of the syringe, however, there exists no apparent means for limiting its withdrawal.

A movable shield member, disclosed in U.S. Pat. No. 5,061,251, issued Oct. 29, 1991 to Paul R. Juhasz, is interconnected to a syringe member to prevent accidental needle strikes when a syringe device is not in use. The shield member is manually movably to expose the needle and is spring biased to shield the needle.

Yet another single-use syringe is disclosed in U.S. Pat. No. 5,084,029, issued Jan. 28, 1992 to Carla Nacci née Tagliaferri et al., wherein the syringe has a needle which retracts into the barrel of the syringe upon a depression of the plunger.

None of the above inventions and patents, taken either singly or in combination, is seen to describe the instant invention as claimed.

SUMMARY OF THE INVENTION

The present invention is a single-use syringe having a needle which retracts upon a full depression of its plunger, rendering the syringe non-reusable. The syringe includes a forward assembly having a stationary housing and a barrel, and rearward assembly. The forward assembly matingly and selectively engages the rearward assembly so as to limit the withdraw or the rearward travel of the plunger relative to the barrel, and to retract the needle upon fully depressing the plunger into the barrel. The syringe may include a cap engageable with the forward end of the stationary housing to sheath the needle prior to use.

The stationary housing comprises a pair of outer and inner side walls bounding a pair of outer cavities and a central cavity. The outer cavities each receive a spring and the central cavity receives the barrel. Further, a peripheral wall extends forwardly of and communicates with the central cavity, and is also configured to receive the barrel. The bore terminates in an annular flange at its forward end, forming an opening for the needle to pass therethrough.

The barrel includes a cylindrical portion having a bore passing therethrough. The bore is configured to cooperatively receive the piston of the plunger. The rearward end of the barrel has a first pair of formations extending therefrom engageable with a formation on the plunger to limit the rearward travel of the plunger. A second pair of formations extending from the barrel are also engageable with the formation on the plunger upon retraction of the needle of the syringe. The cylindrical portion is integral with the nose of the barrel and has a central bore passing therethrough which permits fluid to flow to and from the cylindrical portion through the needle. A first annular groove is provided in the rearward end of the nose for receiving a split ring. The split ring is contractible to permit a rearward displacement of the barrel relative to the stationary housing. The contraction of the split ring is induced by a rearwardly directed force produced by the compression of the coil springs upon a depression of the plunger beyond a predetermined threshold. To terminate the travel of the barrel relative to the stationary body, dogs located proximate the forward end of the nose are engageable with the second annular notches in the station housing.

The plunger is integral with the rearward assembly. A pair of outer and inner arms are integral with and extend longitudinally and forwardly of the plunger. The inner arms are spaced apart a predetermined distance from the pair of outer arms. A piston is disposed intermediate the outer and inner arms along the central axis of the plunger. The outer cavities of the stationary housing are each configured to receive a respective one of the inner arms and upon an axial displacement of the plunger, compress the springs disposed therein. The inner arms are received in the central cavity between the inner side walls and the barrel. The formations on the plunger extend from the inner arms so as to engage the formations on the barrel to limit the rearward travel of the plunger relative to the barrel and to retract the needle upon a depression of the plunger beyond a predetermined threshold. The forward end of the piston includes an annular seal dimensioned and configured to engage the smooth inner surface of the bore of the barrel.

In use, the plunger is withdrawn until the formations thereon engage the rearward formations on the barrel, thus filling the barrel with the predetermined amount of fluid. Since the split ring maintains the barrel in a fixed position relative to the stationary housing, the travel of the plunger is likewise limited with respect to the stationary housing. After the barrel is filled, the fluid is discharged by depressing the plunger. As the plunger is depressed, the springs are compressed and formations on the arms cam against and forwardly beyond the forward most formations on the barrel. Upon a full depression of the plunger, the coil springs are compressed beyond a predetermined threshold and upon release of the plunger, the force of the springs impinges upon the outer arms of the plunger, displacing the plunger and, in turn, the barrel rearwardly, retracting the needle into the stationary housing.

Accordingly, it is a principal object of the invention to provide a single-use syringe having a needle which retracts upon a full depression of its plunger, rendering the syringe non-reusable.

It is another object that the plunger selectively engage the barrel of the syringe so as to limit the withdraw or the rearward travel of the plunger relative to the barrel It is a further object that the syringe include a cap for sheathing the needle prior to use.

Still another object is that the barrel have formations extending therefrom which selectively and matingly engage formations extending from the plunger to limit the travel of the plunger relative to the needle and to retract the needle to a concealed position.

Yet another object is that the barrel have a nose which carries a retaining device which is contractible to permit a rearward displacement of the barrel relative to the stationary housing upon a full depression of the plunger.

It is a another object that the travel of the barrel relative to the stationary body be terminated by detents located proximate the forward end of the nose which are engageable with the stationary housing.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
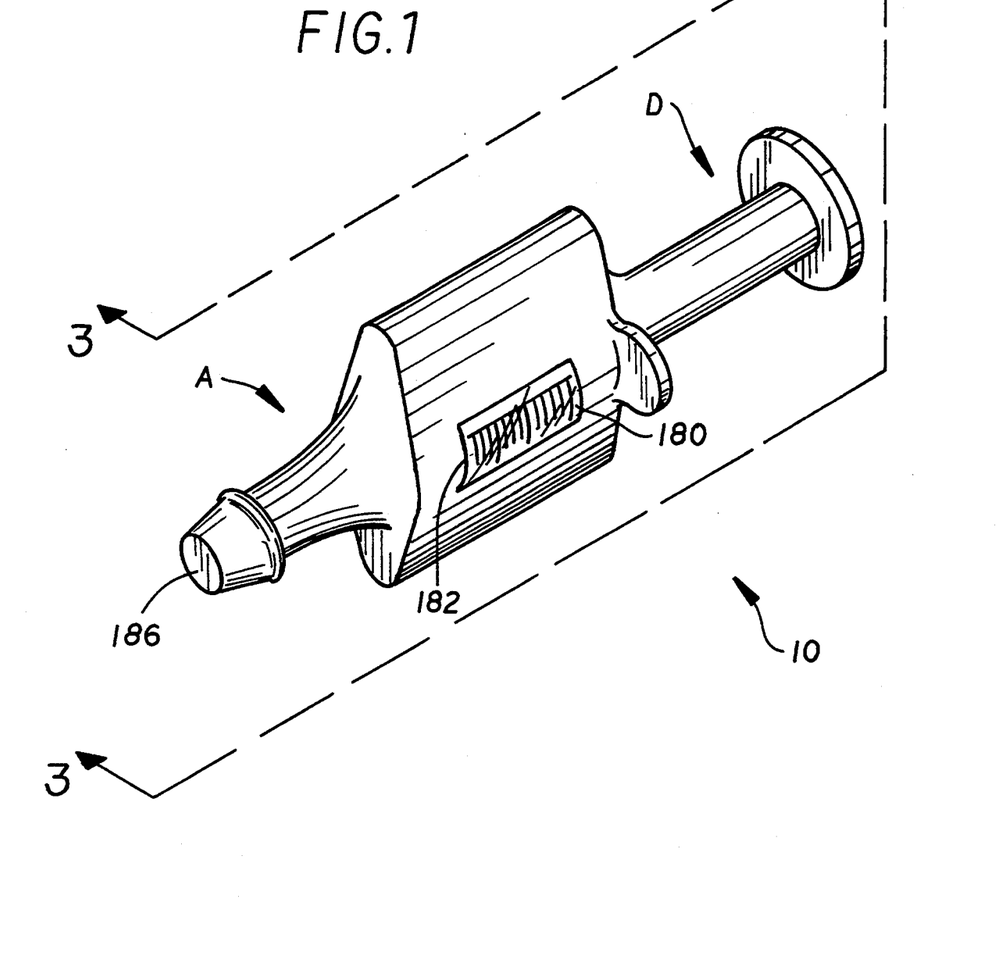
FIG. 1 is a perspective view of a single-use syringe according to the present invention.
Figure 2:
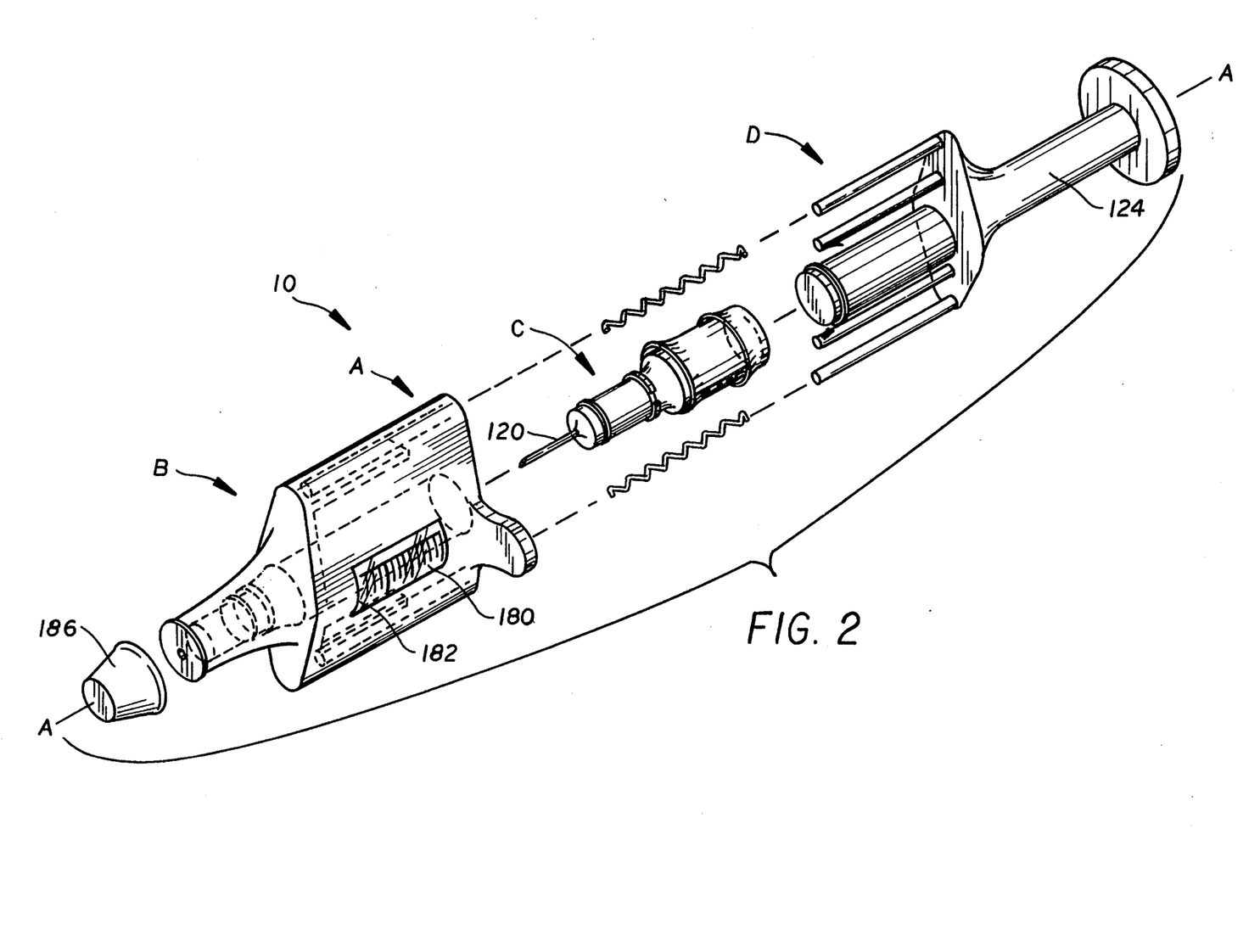
FIG. 2 in an exploded perspective view of the syringe shown in FIG. 1.

The present invention, as shown in FIGS. 1 and 2, is a single-use syringe 10 having a needle which retracts upon a full depression of its plunger 124, rendering the syringe 10 non-reusable. The syringe 10 includes a forward assembly A having a stationary housing B and a barrel C, and rearward assembly D. The forward assembly A matingly and selectively engages the rearward assembly B so as to limit the withdraw or the rearward travel of the plunger 124 relative to the barrel C and to retract the needle 120 upon fully depressing the plunger 124 into the barrel C. A cap 186 is provided to shield the needle 120, shown in FIGS. 1 through to protect a user (not shown) against accidental needle strikes prior to use of the same.

Figure 3:
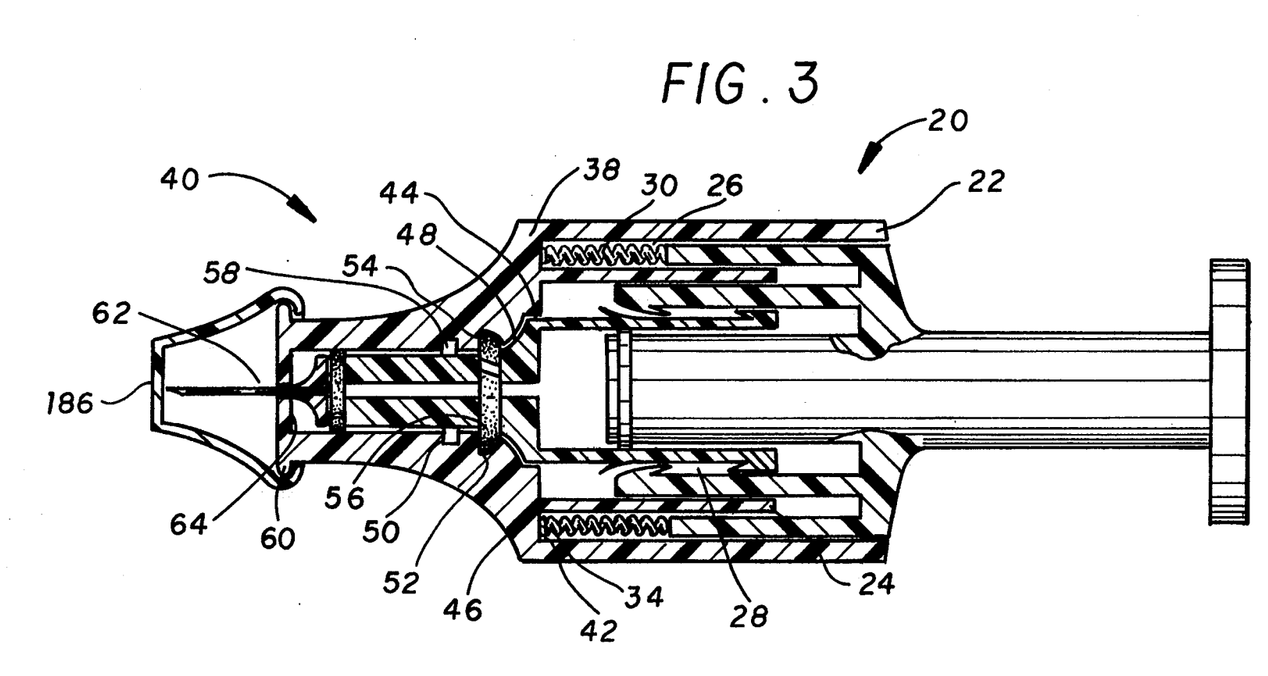
FIG. 3 is a partial cross sectional view of the syringe drawn along lines 3—3 of FIG. 1.
Figure 10:
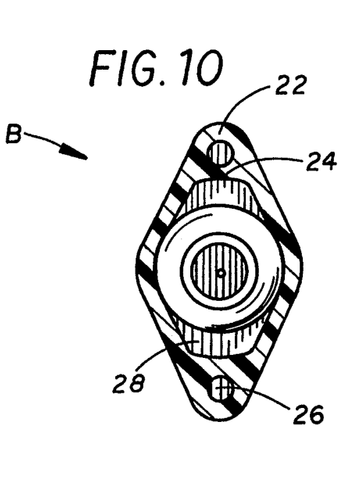
FIG. 10 is a top plan of the stationary housing of the syringe.

As is shown in FIGS. 3 and 10, the stationary housing B comprises a proximal end 20 and a distal end 40. The proximal end 20 includes a pair of longitudinally extending outer side walls 22 and a pair of longitudinally extending inner side walls 24. Each of the side walls 22, 24 are arranged laterally adjacent to, or radial of, the central axis of the stationary housing B. A pair of outer cavities 26 are bounded between respective outer side walls 22 and inner side walls 24, and a central cavity 28 is bounded between the inner side walls 24. The outer cavities 26 are each configured to receive a longitudinally disposed coil spring 30. The side walls 22, 24 are integral with and extend perpendicularly from the distal end 40 of the stationary housing B. The rearward end of the distal end 40 of the stationary housing B provides a supporting surface 42 for supporting the base 34 of the coil spring 30. The rearward end further includes a central recess 44 arranged concentrically with the central cavity 28. A peripheral wall 46 extending forwardly from the rearward end defines a central bore 48 for receiving the barrel C. The interior surface 50 of the rearward end of the bore 48 includes a first annular notch 52 formed by a cam surface 54 and a laterally extending surface 56. A second annular notch 58 is also formed within the interior surface of the bore 48 forward of the first annular notch 52. The bore 48 terminates in an annular flange 60 at the forward end of the distal end 40 of the stationary housing B. The annular flange 60 forms an opening 62 in the forward end of the distal end 40 of the stationary housing B as well as provides a retaining surface 64 for limiting the forward travel of the barrel C through the bore 48. Portions of the stationary housing B other than the portion about the cylindrical portion 70 of the barrel C are preferably fabricated of an opaque material so as to conceal the components therein as well as the interactive relationship of the same. The portion of the stationary housing B about the cylindrical portion 70 of the barrel C is preferably fabricated of a transparent or translucent material so as to permit a visual observation of the contents of the barrel C therethrough. Volumetric indicia 180 is disposed along the transparent potion of the stationary housing B to gauge the amount of fluid (not shown) entering and leaving the barrel C. In addition, a visual indicator 182 is disposed along the transparent portion of the stationary housing B for providing an indication of how far forward the plunger 124 may be depressed relative to the barrel C before causing the needle 120 to be retracted into the stationary housing B.

Figure 5:
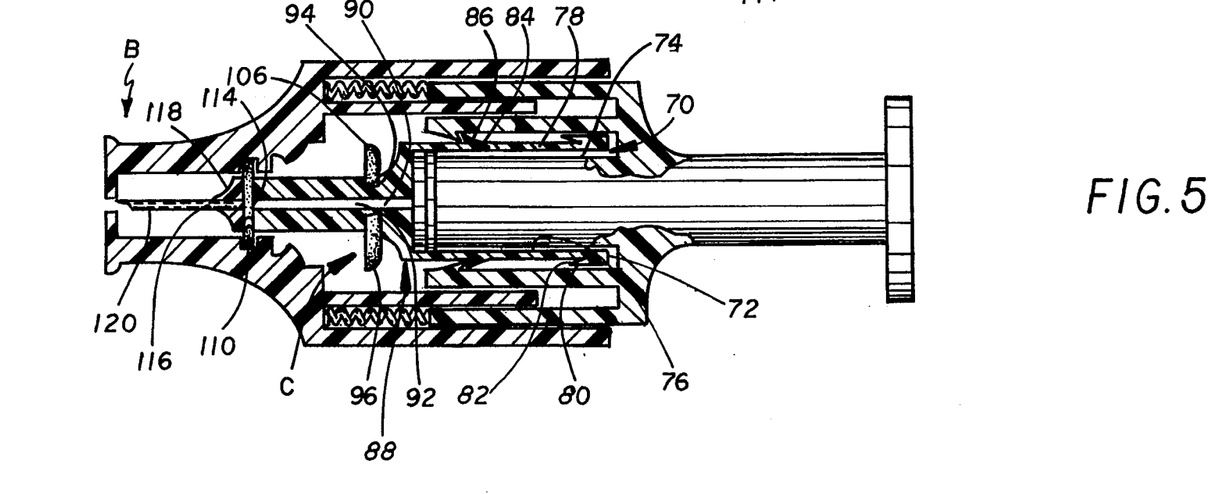
FIG. 5 is a partial cross sectional view of the syringe with the needle retracted.
Figure 6:
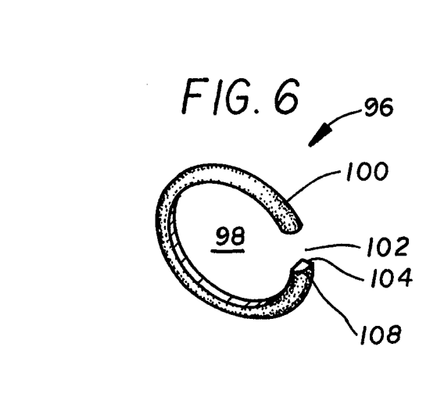
FIG. 6 is a perspective view of the split ring.
Figure 7:
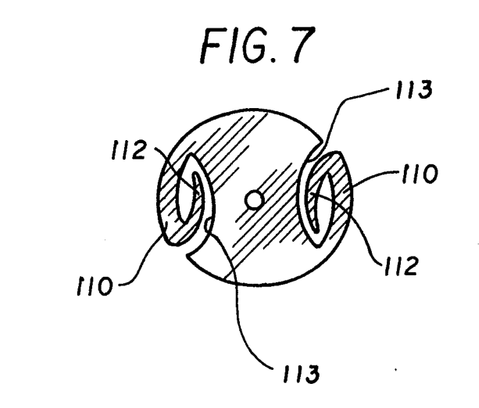
FIG. 7 is a top plan of the dog ear arrangement.

Now referring to FIG. 5, the barrel C includes a rearwardly disposed cylindrical portion 70 having an opening 72 at its proximal end and a bore 74 with a smooth inner surface 76 passing therethrough. The bore 74 is bounded by a peripheral wall 78. The opening 72 and the bore 74 are configured to cooperatively receive the piston 138 of the plunger 124. The rearward end of the cylindrical portion 70 has a first projection or formation 80, such as the annular projection shown, extends from the peripheral wall 78 of the cylindrical portion 70 and is directed radially outward from the central axis of the barrel C. The formation 80 includes a forwardly directed stop surface 82 engageable with formations 140 of the plunger 124 to be disclosed hereinafter. The stop surface 82 limits the rearward travel of the plunger 124. A second formation 84, such as the annular projection shown, extends radially outward from the peripheral wall 78 of the cylindrical portion 70 a predetermined distance from the forward end thereof. This second formation 84 includes a locking surface 86 engageable with the formations 140 of the plunger 124 to retract the needle 120 of the syringe 10. The first and second formations 80, 84 are concentrically aligned along a common axis A—A, as shown in FIG. 2. The cylindrical portion 70 is integral with and extends axially from the nose 88 of the barrel C. An opening 90 in the rearward end of the nose 88 communicates with a central bore 92 which passes through the nose 88. A first annular groove 94 is provided in the nose 88 adjacent the rearward end thereof for receiving a split ring 96. The split ring 96, as is shown in FIG. 6, has a central opening 98 bounded by a C-shaped body 100 having a slot 102 extending radially therethrough from the opening 98 to the outer periphery of the C-shape body 100. The C-shaped body 100 further includes a flat forward surface 104 for engaging a forwardly disposed planar surface 106 of the first annular groove 94 and a curved rearward camming surface 108 for cammingly engaging the complementary rearwardly disposed curved camming surface 54 of the first annular notch 52 in the distal end 40 of the stationary housing B. The first annular groove 94 has a depth which permits the split ring 96 to contract inward camming along first annular notch 52 in the distal end 40 of the stationary housing B until the outer periphery of the C-shaped body 100 is small enough so as to escape therefrom and permit a rearward displacement of the barrel C relative to the stationary housing B. The contraction of the split ring 96 is induced by a rearward directed force produce by depression of the plunger 124 forwardly beyond the visual indicator 182 which, in turn, compresses the coil springs 30 beyond a predetermined threshold. To limit the rearward travel of the barrel C relative to the stationary housing B, opposingly direct dogs 110 located at the forward end of the nose 88 are engageable with the second annular notch or dog notch 58. The dogs 110 may be formed integrally with the nose 88. As is shown in FIG. 7, a biasing member 112 is integral with each dogs 110 and is cammingly engageable with a camming surface 113 to bias the dogs 110 normally and radially outward. The interior surface 50 of the central bore 48 of the distal end of the stationary housing B maintains each biasing member 112 and, in turn, each dog 110 in a compressed state until the nose 88 is rearwardly displaced to the point where the dogs 110 enter into the second annular notches 58, at which point the travel of the barrel C, both forward and rearward, is terminated. The central bore 92 passing through the nose 88 of the barrel C terminates at an opening 114 at the forward end of the nose 88 and communicates with a bore 116 passing through a hub 118 and needle 120 arrangement attached to the forward end of the nose 88. The cylindrical portion 70 of the barrel C is preferably fabricated of a transparent or translucent material so as to permit its contents to be visually observed therethrough.

Figure 4:
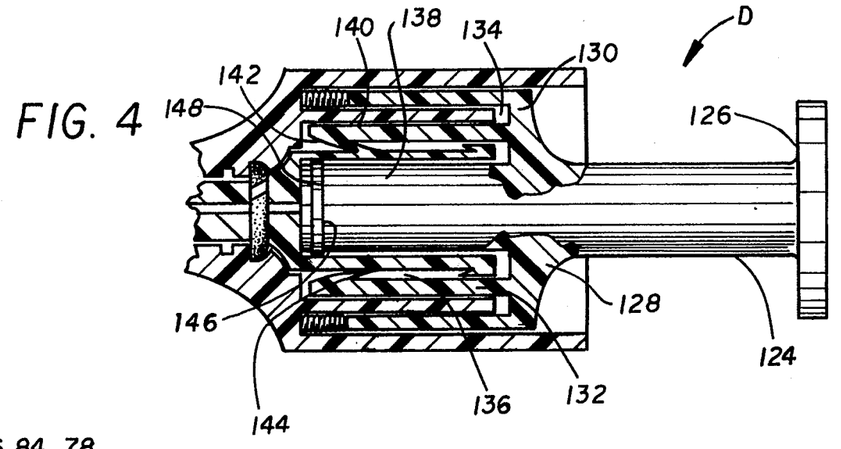
FIG. 4 is a fragmentary, partial cross sectional view of the syringe with the plunger fully depressed.

Referring to FIG. 4, the rearward assembly D includes a plunger 124 having a handle 126 at its distal end for assisting in the displacement of the same. Intermediate the plunger 124 are oppositely disposed, laterally or radially extending branch elements 128. A pair of outer arms 130 are integral with and longitudinally extend forwardly from the terminal ends of the branch elements 128. A pair of inner arms 132 are integral with and extend longitudinally forwardly from the branch elements 128 and are spaced apart a predetermined distance from and interiorly of the pair of outer arms 130. A longitudinally disposed, piston 138 is integral with and extends forwardly from the branch elements 128 spaced equidistantly between the pair of inner arms 132 and along the central axis of the plunger 124. A pair of outer cavities 134 are bounded between respective outer arms 130 and inner arms 132, and a pair of inner cavities 136 are bounded between the piston 138 and the inner arms 132. The outer cavities 134 are each configured to receive a respective one of the inner side walls 24 of the stationary housing B which axially and slidably engage the same when the outer arms 130 are slidably received by respective outer cavities 26 of the stationary housing B. The inner cavities 136 are each configured to receive the cylindrical portion 70 of the barrel C. A formation 140 extends radially inward from the forward end of each of the inner arms 132. Each formation 140 has an inwardly facing camming surface 142 for cammingly engaging a respective one of the second pair of formations 84 extending from the cylindrical portion 70 of the barrel C. Each formation 140 further includes a rearwardly directed surface 144 for selectively engaging the stop surface 82 of the first formation 80 and the locking surface 86 of the second formation 84 to limit the rearward travel of the plunger 124 and retract the barrel C, respectively. The forward end of the piston 138 includes an annular groove 146 for receiving an annular seal 148. The piston 138 is slidably and axially received by the central bore 74 of the barrel C and the annular seal 148 is dimensioned and configured to engage the smooth inner surface 76 so as to provide a seal between the piston 138 and the barrel C.

Figure 8:
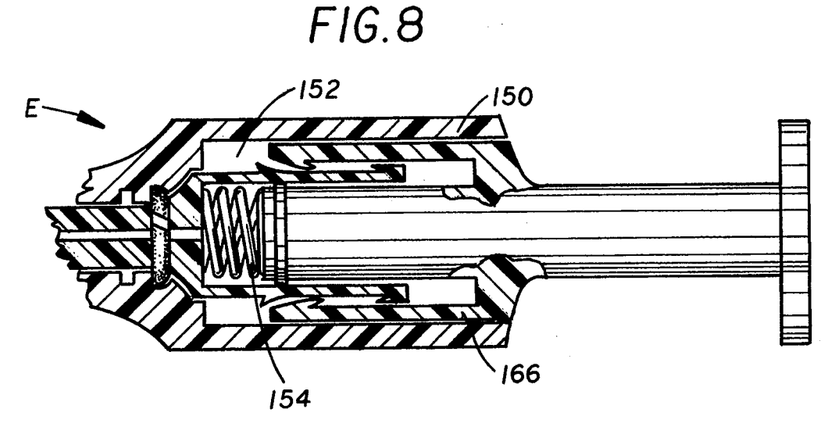
FIG. 8 is a fragmentary, partial cross sectional view of an alternative embodiment of the single-use syringe.
Figure 9:
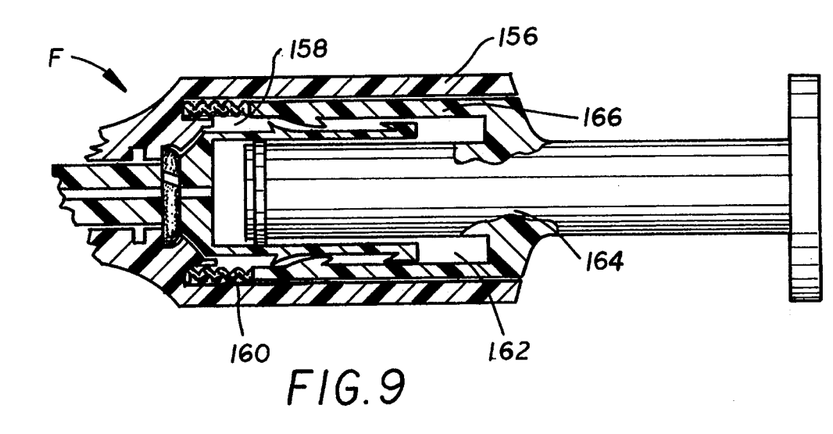
FIG. 9 is a fragmentary, partial cross sectional view of another alternative embodiment of the single-use syringe.
Figure 13:
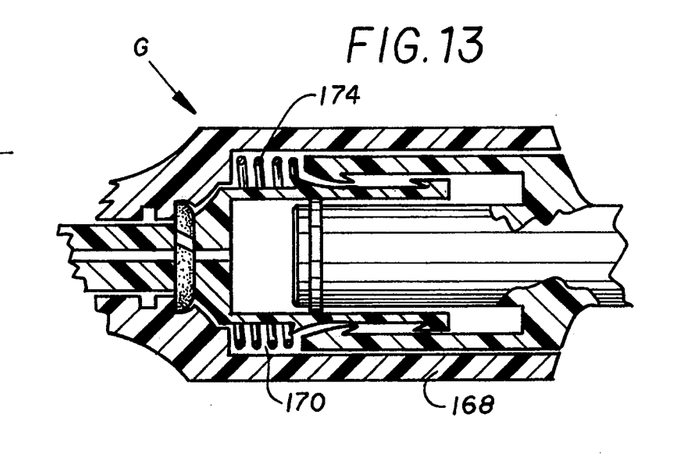
FIG. 13 is a fragmentary, partial cross-sectional view of another alternative embodiment of the single-use syringe.

It should be noted that the present invention is not limited to the configuration shown in FIGS. 1 through 5, but may be configured in numerous fashions, such as is shown in FIGS. 8, 9 and 13. FIGS. 8, 9 and 13 show alternative embodiments wherein the stationary housings E, F, G each include only outer side walls 150, 156, 168 bounding a central cavity 152, 158, 170. In FIG. 8, a single coil spring 154 is shown to be disposed in the barrel C. In FIG. 9, a pair of coil springs 160 are disposed in the central cavity 158 adjacent the outer side walls 156. In yet another alternative, as is shown in FIG. 13, a single coil spring 174 can be disposed in the cavity 170 formed between the outer side walls 156 and the piston 164. In these embodiments, the rearward assembly, not shown, is only required to have an outer pair of arms 166.

Figure 11:
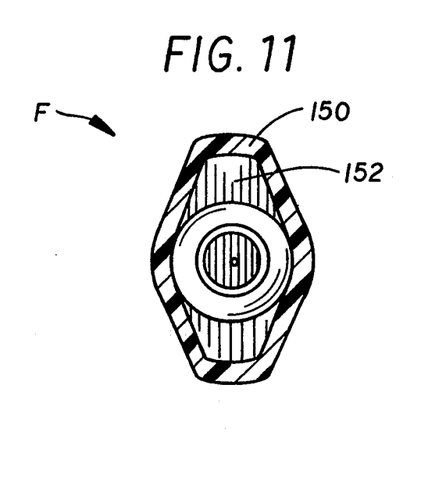
FIG. 11 is a top plan of an alternative stationary housing of the syringe.
Figure 12:
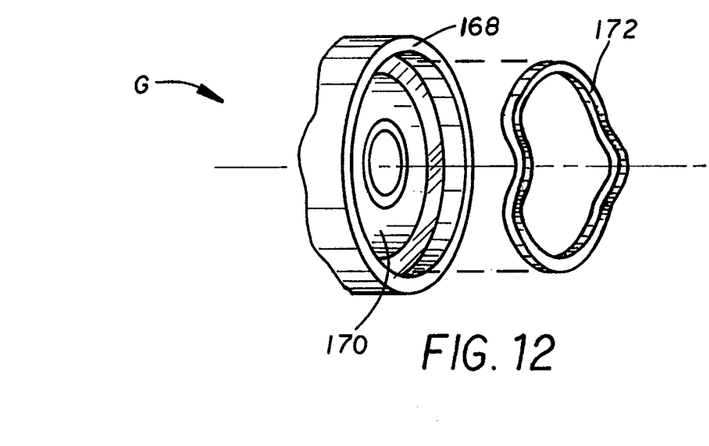
FIG. 12 is a fragmentary perspective view of another alternative stationary housing of the syringe.

It should also be understood that the shape of the stationary housing B, E, F, G present invention is not limited to that shown in FIGS. 1, 2 and 10 or shown in FIGS. 8, 9 and 11. FIGS. 12 and 13 shows an alternative stationary housing G which is cylindrical in shape, as opposed to being non-cylindrical, and in this embodiment has only an outer side wall 168 bounding a central cavity 170. A resilient ring 172, as opposed to a coil spring, may be received by the central cavity 170. In this embodiment, the rearward assembly (not shown) has a cylindrical shape which is complementary to that of stationary housing G. The resilient ring 172 would seat within the central cavity 170 and the distal end of the outer wall of the rearward assembly would compress the resilient ring 172 in a manner similar to that of the aforementioned embodiments.

In operation, the cap 186, shown in FIG. 1, is removed to expose the needle 120. The plunger 124 is depressed until the annular seal 148 thereof reaches but does not extend beyond the visual indicator 182. This indicator 182 aids the user in making a judgement as to how far the plunger 124 may be depressed prior to causing the needle 120 to retract. This enables the user to maximize the volume within the barrel C. From this depressed position, the plunger 124 may be withdrawn to fill the barrel C with a desired amount of fluid (not shown), as may be gauged by the volumetric indicia 180 arranged along the stationary housing B, as is shown in FIG. 1, or until the formations 140 on the plunger 124 engage the rearward formation 80 on the barrel C, filling the barrel C to its capacity. Because the split ring 96 maintains the barrel C in a fixed position relative to the stationary housing B, the travel of the plunger 124 is likewise limited with respect to the stationary housing B. After the barrel C is filled, the fluid is discharged by depressing the plunger 124. As the plunger 124 is depressed, the coil springs 30 are compressed and formations 140 on the arms 132 cam against and forwardly beyond the forward most formations 84 on the barrel C, as is shown in FIG. 4. Upon a full depression of the plunger 124, the seal 148 is displaced beyond the visual indicator 182 and the coil springs 30 are compressed beyond a predetermined threshold. Upon release the plunger 124, the force of the coil springs 30 impinges upon the outer arms 130 of the plunger 124, displacing the plunger 124 and, in turn, the barrel C rearwardly, retracting the needle 120 into the stationary housing B, as is shown in FIG. 5.

It is to be understood that the present invention is not limited to the embodiments described above, but encompasses any and all embodiments within the scope of the following claims.

I claim:

1. A single-use syringe comprising:
    a forward assembly including:
        a housing,
        a barrel having a needle disposed at a distal end thereof and having a cylindrical bore passing therethrough; and
        means for fixing said barrel within said housing in accordance with a first condition, said barrel and said needle being retractable into said housing in accordance with a second condition,
    a plunger having a piston disposed at a distal end thereof, said piston slidably engaging said cylindrical bore passing through said barrel;
    means for limiting axial displacement of said plunger relative to said barrel; and
    means for retaining said barrel and said needle in a retracted posture within said housing, wherein said retaining means includes a locking member for interlocking said barrel and said housing.

2. The single-use syringe according to claim 1, wherein said barrel includes a first formation and said plunger includes a second formation, said first formation being cooperatively engageable with said second formation to form said limiting means.

3. The single-use syringe according to claim 1, further including means for retracting said barrel and said needle into said housing in accordance with the second condition, and wherein
    said barrel includes a first formation and said plunger includes a second formation, said first formation being cooperatively engageable with said second formation.

4. The single-use syringe according to claim 3, further including an arm movable with said plunger, and wherein
    said retracting means includes a spring compressible between said housing and said plunger, said arm being movable so as to operate and compress said spring upon depression of said plunger.

5. A single-use syringe, comprising:
    a forward assembly including:

a housing,
a barrel having a needle disposed at a distal end thereof and having a cylindrical bore passing therethrough, said barrel including a first formation; and
a split ring for fixing said barrel within said housing in accordance with a first condition, said split ring being mutually engageable with said housing and said barrel, said split ring further being contractible to disengage from said housing so as to permit said barrel to be retracted;
a plunger having a piston disposed at a distal end thereof, said piston slidably engagable with said cylindrical bore passing through said barrel, and said plunger having a second formation, said first formation being cooperatively engageable with said second formation,
means for limiting axial displacement of said plunger relative to said barrel;
means for retracting said barrel and said needle into said housing in accordance a second condition; and
means for retaining said barrel and said needle in a retracted posture within said housing.

6. The single-use syringe according to claim 1, further including a cap which is releasably mountable on an end of said housing.

7. The single-use syringe according to claim 1, further including indicia disposed on said housing, said indicia including a plurality of graduation marks for gauging a level in which said barrel is filled.

8. The single-use syringe according to claim 1, further including indicia disposed on said housing, said indicia including a mark for gauging a position of said plunger relative to said barrel.

9. The single-use syringe according to claim 1, further including means for retracting said barrel and said needle into said housing in accordance with the second condition.

10. The single-use syringe according to claim 1, wherein said housing includes a distal end and an inner surface, and wherein
said locking member includes:
an annular notch formed in said inner surface of said housing a predetermined distance from said distal end thereof;
a dog formed integrally with said barrel proximate the distal end of said barrel, said dog having a camming surface slidably engageable with said inner surface of said housing and matingly engageable with said annular notch in said inner surface of said housing;
a biasing member integral with said dog for biasing said dog against said inner surface of said housing in accordance with the first condition and for biasing said dog into said annular notch in said inner surface of said housing in accordance with the second condition.

11. The single-use syringe according to claim 5, wherein said retracting means includes a spring compressible between said housing and said plunger.

12. The single-use syringe according to claim 11, further including an arm movable with said plunger so as to operate and compress said spring upon depression of said plunger.

13. The single-use syringe according to claim 5, wherein said retaining means includes a locking member for interlocking said barrel and said housing.

14. The single-use syringe according to claim 13, wherein said housing includes a distal end and an inner surface, and wherein
said locking member includes:
an annular notch formed in said inner surface of said housing a predetermined distance from said distal end thereof;
a dog formed integrally with said barrel proximate the distal end of said barrel, said dog having a camming surface slidably engageable with said inner surface of said housing and matingly engageable with said annular notch in said inner surface of said housing;
a biasing member integral with said dog for biasing said dog against said inner surface of said housing in accordance with the first condition and for biasing said dog into said annular notch in said inner surface of said housing in accordance with the second condition.

15. The single-use syringe according to claim 5, further including indicia disposed on said housing, said indicia including a plurality of graduation marks for gauging a level in which said barrel is filled.

16. The single-use syringe according to claim 5, further including indicia disposed on said housing, said indicia including a mark for gauging a displacement of said plunger relative to said barrel.

17. The single-use syringe according to claim 5, further including a cap which is releasably mountable on an end of said housing.

18. A single-use syringe comprising:
a forward assembly including:
a housing,
a barrel having a needle disposed at a distal end thereof and having a cylindrical bore passing therethrough, said barrel including a first formation; and
a split ring for fixing said barrel within said housing in accordance with a first condition, said split ring being mutually engageable with said housing and said barrel, said split ring further being contractible to disengage from said housing so as to permit said barrel to be retracted;
a plunger having a piston disposed at a distal end thereof, said piston slidably engagable with said cylindrical bore passing through said barrel, and said plunger having a second formation, said first formation being cooperatively engageable with said second formation,
means for limiting axial displacement of said plunger relative to said barrel; and
means for retaining said barrel and said needle in a retracted posture within said housing.

19. A single-use syringe comprising:
a forward assembly including:
a housing,
a barrel having a needle disposed at a distal end thereof and having a cylindrical bore passing therethrough; and
means for fixing said barrel within said housing in accordance with a first condition, said barrel and said needle being retractable into said housing in accordance with a second condition,
a plunger having a piston disposed at a distal end thereof, said piston slidably engaging said cylindrical bore passing through said barrel;
means for limiting axial displacement of said plunger relative to said barrel;

means for retaining said barrel and said needle in a retracted posture within said housing;

means for retracting said barrel and said needle into said housing in accordance with the second condition, and wherein said barrel includes a first formation and said plunger includes a second formation, said first formation being cooperatively engageable with said second formation; and an arm movable with said plunger, and wherein said retracting means includes a spring compressible between said housing and said plunger, said arm being movable so as to operate and compress said spring upon depression of said plunger.

* * * * *